United States Patent [19]

Johnson et al.

[11] Patent Number: 5,411,647
[45] Date of Patent: May 2, 1995

[54] TECHNIQUES TO IMPROVE THE PERFORMANCE OF ELECTROCHEMICAL SENSORS

[75] Inventors: Kirk W. Johnson; John J. Mastrototaro, both of Indianapolis, Ind.

[73] Assignee: Eli Lilly and Company, Indianapolis, Ind.

[21] Appl. No.: 187,121

[22] Filed: Jan. 25, 1994

Related U.S. Application Data

[63] Continuation of Ser. No. 980,465, Nov. 23, 1992, abandoned.

[51] Int. Cl.⁶ .......................................... G01N 27/26
[52] U.S. Cl. .......................... 204/153.1; 204/153.12; 204/402; 204/412
[58] Field of Search ............... 204/153.12, 402, 153.1, 204/412, 403, 400

[56] References Cited

U.S. PATENT DOCUMENTS 4,935,105  6/1990  Churchouse .................. 204/153.12

OTHER PUBLICATIONS

M. Koudelka, F. Rohner-Jeanrenaud, J. Terrettaz, E. Bobbioni-Harsch, N. F. de Rooij & B. Jeanrenaud, "In-Vivo Behaviour of Hypodermically Implanted Microfabricated Glucose Sensors," *Biosensors & Bioelectronics* 6 (1991), pp. 31-36.

G. Velho, P. Forguel, R. Sternberg, D. R. Thevenot & G. Reach, "In Vitro and In Vivo Stability of Electrode Potentials in Needle-Type Glucose Sensors," *Diabetes* 38 (1989), pp. 164-171.

K. Rebrin, U. Fischer, T. V. Woedtke, P. Abel & E. Brunstein, "Automated Feedback Control of Subcutaneous Glucose Concentration in Diabetic Dogs," *Diabetologia* 32 (1989), pp. 573-576.

M. Josowicz, J. Janata, M. Levy, "Electrochemical Pretreatment of Thin Film Platinum Electrodes," *J. Electrochem. Soc.*, 135-1 (1988), pp. 112-115.

P. Tuzhi, L., Honghuan, L. Guoqin, C. Uping, "Constant Potential Pretreatment of Carbon Fiber Electrodes for In Vivo Electrochemistry," *Analytical Letters*, 24-N6 (1991), pp. 935-945.

J. D. Roth, M. J. Weaver, "The Electrooxidation of Carbon Monoxide on Platinum as Examined by Surface Infrared Spectroscopy under Forced Hydrodynamic Conditions" *J. Electroanal. Chem.*, 307 (1991), pp. 119-137.

J. Mastrototaro, K. W. Johnson, R. J. Morff, D. Lipson, C. C. Andrew, D. J. Allen, "An Electroenzymatic Glucose Sensor Fabricated on a Flexible Substrate," *Sensors and Actuators Chem.* B 5:1-4 (1992), pp. 139-144.

K. W. Johnson, "Reproducible Electrodeposition of Biomolecules for the Fabrication of Miniature, Electroenzymatic Biosensors," *Sensors and Actuators Chem.* B 5:1-4 (1991), pp. 85-89.

J. Wang, L. D. Hutchins, "Activation of Glassy Carbo Electrodes by Alternating Current Electrochemical Treatment," *Anal. Chim. Acta* 167 (1985), pp. 325-334.

R. C. Engstrom, "Electrochemical Pretreatment of Glassy Carbon Electrodes," *Anal. Chem.* 54 (1982), pp. 2310-2314.

R. C. Engstrom, V. A. Strasser, "Characterization of Electrochemically Pretreated Glassy Carbon Electrodes," *Anal. Chem.* 56 (1984), pp. 136-141.

(List continued on next page.)

*Primary Examiner*—John Niebling
*Assistant Examiner*—Bruce F. Bell
*Attorney, Agent, or Firm*—Woodard, Emhardt, Naughton, Moriarty & McNett

[57] ABSTRACT

A method of improving the utility of electrochemical glucose sensors by decreasing either or both their settling time and their sensitivity to interfering compounds. In particular, the settling time of an electrochemical glucose sensor is improved by pretreating the operating electrode with a negative electric current at a constant current density. The sensor's sensitivity to intefering compounds is reduced by operating the sensor at a reduced voltage while the glucose concentration measurement is being made.

31 Claims, 9 Drawing Sheets

OTHER PUBLICATIONS

G. Palleschi, M. A. N. Rahni, G. J. Lubrano, J. N. Ngwainbi, G. G. Guilbault, "A Study of Interferences in Glucose Measurements in Blood by Hydrogen Peroxide Based Glucose Probes," *Anal. Biochem.* 159 (1986), pp. 114–121.

G. Sittampalam, G. S. Wilson, "Surface-Modified Electrochemical Detector for Liquid Chromatography," *Anal. Chem.* 55 (1983), pp. 1608–1610.

D. S. Bindra, Y. Zhang, G. S. Wilson, R. Sternberg, D. R. Thevenot, D. Moatti, G. Reach, "Design and In Vitro Studies of a Needle-Type Glucose Sensor for Subcutaneous Monitoring," *Anal. Chem.* 63 (1991), pp. 1692–1696.

D. J. Harrison, R. F. B. Turner, H. P. Baltes, "Characterization of Perfluorosulfonic Acid Polymer Coated Enzyme Electrodes and a Miniaturized Integrated Potentiostat for Glucose Analysis in Whole Blood," *Anal. Chem.* 60 (1988), pp. 2002–2007.

S. V. Sasso, R. J. Pierce, R. Walla, A. M. Yacynych, "Electropolymerized 1,2–Diaminobenzene as a Means to Prevent Interferences and Fouling and to Stabilize Immobilized Enzyme in Electrochemical Biosensors," *Anal. Chem.* 62 (1990), pp. 1111–1117.

L. C. Clark, Jr., E. W. Clark, "Differential Anodic Enzyme Polarography for the Measurement of Glucose," *Adv. Exp. Med. Biol.*, 37A (1973), pp. 127–133.

R. Maidan, A. Heller, "Elimination of Electrooxidizable Interferants in Glucose Electrodes," *J. Am. Chem. Soc.* 113 (1991), pp. 9003–9004.

S. J. Yao, W. Xu, S. K. Wolfson, Jr., "The Infernece of Ascorbate and Urea in Low–Potential Electrochemical Glucose Sensing," *Proc. Int. Conf. IEEE Eng. Med. Biol. Soc.* 12 (1990), pp. 0487–0489.

TECHNIQUES TO IMPROVE THE PERFORMANCE OF ELECTROCHEMICAL SENSORS

This application is a continuation of application Ser. No. 07/980,465, filed Nov. 23, 1992, now abandoned.

FIELD OF THE INVENTION

This invention relates generally to electrochemical sensors, and more particularly to methods for improving the performance of glucose oxidase-based electrochemical sensors by reducing their settling time and their sensitivity to interfering compounds.

BACKGROUND OF THE INVENTION

One of the major impediments to the commercialization of an amperometric sensor, particularly an enzymatic glucose sensor, is its settling time. Settling time is the amount of time necessary for the current output from the sensor to settle to a stable value following the initial application of the potential to the sensor. During this time, the electrical double layer at the surface of the working and counter electrodes is charged and faradaic reactions are established.

With amperometric, electroenzymatic glucose sensors, settling times can take up to several hours. For example, Koudelka et al. have reported a 90-minute settling time following in-vivo implantation. Koudelka, Rohner-Jeanrenaud, Terrettaz, Bobbioni, Rooij & Jean-renaud, *In-Vivo Behavior of Hypodermically Implanted Microfabricated Glucose Sensors*, 6 Biosensors & Bioelectronics 31 (1991). Similarly, Velho et al. reported a settling time of at least one hour for an implanted needle-type glucose sensor. Velho, Sternberg, Thevenot & Reach, *In Vitro and In Vivo Stability of Electrode Potentials in Needle-Type Glucose Sensors*, 38 Diabetes 164 (1989). Between two and four hours of settling time were required for an in-vivo sensor fabricated by Rebrin et al. Rebrin, Fischer, Woedtke, Abel & Brunstein, *Automated Feedback Control of Subcataneous Glucose Concentration in Diabetic Dogs*, 32 Diabetologia 573 (1989). Similar settling times have been observed and reported by other investigators. It can be appreciated that these settling times are a disadvantage to the commercialization of an amperometric sensor, and that such settling times may preclude the use of electrochemical sensors in emergency care circumstances.

In one aspect of the present invention, the settling time of an electroenzymatic glucose sensor is reduced by pretreating the working electrode of the sensor. Although such a method has not previously been disclosed, electrochemical pretreatment of electrodes is known for other purposes. For example, electrochemical methods have been used to remove contaminants from the surface of noble metal electrodes, to enhance the sensitivity and selectivity of the electrodes, and to shift the oxidation potential of some compounds. However, the electrochemical pretreatment of an amperometric glucose sensor for the purpose of reducing its settling time is not suggested by such treatments, and has not been heretofore reported.

Another problem encountered with the use of electrochemical sensors to measure the concentration of a particular compound such as glucose is "interference" caused by the oxidation of other compounds in the body. For example, common interfering compounds encountered in in-vivo implantation include ascorbic acid, uric acid, cysteine and acetaminophen. These interfering compounds may cause an erroneous positive offset which is not acceptable when quantifying the glucose levels of individuals with diabetes.

Several methods have been devised to minimize the effects of interfering compounds on electroenzymatic glucose sensors. For example, a regenerated cellulose membrane or a negatively charged cellulose acetate membrane has been incorporated between the working electrode and the enzyme layer covering that electrode. These membranes allow the hydrogen peroxide to permeate the membrane layer, but interfering compounds such as ascorbic acid and uric acid cannot pass due to the size and/or charge exclusion characteristics of the membrane.

In another technique, two electrodes are used. One electrode is covered with an oxidizing enzyme, while the enzyme is denatured or absent from the other electrode. The current from interfering compounds is eliminated by analyzing the difference in current output from the two electrodes.

These techniques for reducing sensor sensitivity to interfering compounds are not attractive because additional membranes and/or electrodes increase the cost to produce the sensors. In addition, including an extra membrane layer to exclude interfering compounds would both increase the response time of the sensor and decrease the magnitude of the current output.

Still another technique incorporates a chemical that is capable of functioning as an electron acceptor in place of oxygen to shuttle electrons from the redox center of the enzyme to the surface of the working electrode. These chemicals are referred to as redox mediators. This type of sensor is reported to be oxygen-insensitive and can function in an anaerobic environment. These compounds have a low redox potential which lessens the chance of interferences from other electroactive compounds. Unfortunately, these compounds are difficult to retain inside the sensor and some are toxic.

A need therefore exists for a method of improving the utility of electrochemical glucose sensors by reducing their settling time and by improving their ability to provide accurate readings of one desired compound despite the presence of interfering compounds. The present invention addresses these needs.

SUMMARY OF THE INVENTION

Briefly describing the present invention, there is provided a method of improving the utility of electrochemical glucose sensors by decreasing both their settling time and their sensitivity to interfering compounds. In particular, the settling time of an electrochemical glucose sensor is improved by pretreating the operating electrode of the sensor by applying a constant current to that electrode. An electrochemical glucose sensor's sensitivity to interfering compounds is reduced by operating the sensor at a reduced voltage when the glucose concentration measurement is being performed.

One object of the present invention is to provide an electrochemical glucose sensor having a reduced settling time.

A further object of the present invention is to provide a method of using an electrochemical glucose sensor which reduces its sensitivity to interfering compounds.

Further objects and advantages of the present invention will be apparent from the following description.

DESCRIPTION OF THE PREFERRED EMBODIMENT

Figure 1:
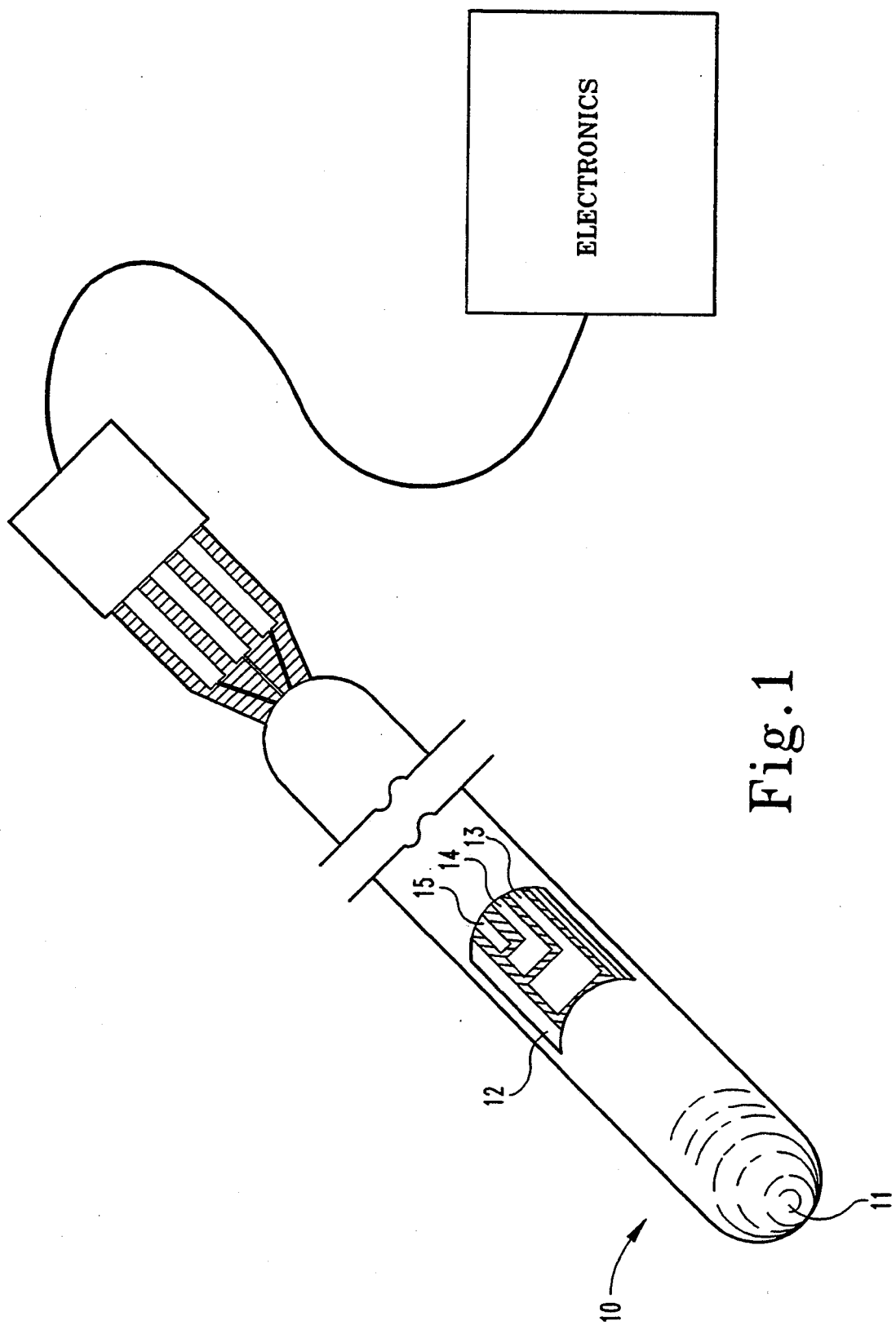
FIG. 1 is a perspective view of the electrochemical glucose sensor of the present invention according to one preferred embodiment.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to a method of improving the performance of electrochemical glucose sensors. In one aspect of the invention, tile settling time of a sensor is reduced by pretreating the working electrode of the sensor with an electric current prior to the sensor's use to measure glucose in a liquid medium. In another aspect of the invention, the sensor's sensitivity to interfering compounds is reduced by operating the sensor at a potential which is significantly less than the +0.6 V typically applied to such sensors. In a third aspect of the invention, the performance of an electrochemical glucose sensor is improved by sequentially utilizing both of the above methods.

The electrochemical glucose sensors used in the preferred embodiments of the present invention were produced according to the techniques described in Mastrototaro, Johnson, Morff, Lipson, Andrew & Allen, *An Electroenzymatic Glucose Sensor Fabricated On A Flexible Substrate*, B 5:1–4 Sensors and Actuators 139–44 (1992) and Johnson, *Reproducible Electrodeposition Of Biomolecules For The Fabrication Of Miniature, Electroenzymatic Biosensors*, B 5:1–4 Sensors and Actuators 85–89 (1992). The glucose sensors are fabricated using integrated-circuit fabrication techniques in order to develop small, reliable, reproducible and manufacturable devices. The sensors are fabricated in batch quantities consisting of four 4"×4" plates having 28 sensors per plate. The processing scheme is fully set forth in U.S. Pat. No. 5,108,819, issued on Apr. 28, 1992, the pertinent portions of which are hereby incorporated by reference. The process may be summarized as follows.

The base substrate for the sensor is a 50 $\mu$m thick layer of DuPont PI-2540 polyimide. The layer is formed by spin-coating the liquid polyimide onto a clean 4" by 4" glass plate and heat curing the resulting layer. This step can be repeated until the desired film thickness is achieved. Several polyimides with different viscosities are available and may be used.

A triple layer of chromium-gold-chromium is sputter-deposited onto the plates and patterned to form the conducting layers of the glucose sensors. The chromium is used as an adhesion promoter between the gold and the polyimide. The metal layers are patterned using a standard photolithographic process. Once the triple layer of metal is patterned, a second photolithography step is used to remove the chromium and expose the underlying gold at the locations where the electrodes will be situated. The resultant layer consists of metallization patterned to form the chromium-gold-chromium conductors of 28 glucose sensors with three gold electrodes per sensor.

The plates are then covered with a 1.2 $\mu$m thick photoimagable polyimide insulation layer (DuPont PI-2703D), which is patterned to expose the active regions of the underlying gold electrodes. The polyimide is spin-coated in a liquid form onto each plate. It is then prebaked, exposed to UV light to pattern the layer, spray developed, rinsed and heat cured.

The plates are immersed in distilled deionized (DI) water for between 8 and 24 hours to remove the sheet of sensors from the glass plate. The procedure can be accelerated by boiling the water. Once completely free from the plate, the sheet of sensors is cut into 'quarter sheets' consisting of seven sensors per sheet. A microscopic inspection of the sensors is then performed to determine which devices are structurally sound. Sensors with defects are logged appropriately and are not plated in the following procedures.

The working and counter electrodes of the sensor are electroplated with Pt-black and the reference electrode is plated with Ag/AgCl. Glucose oxidase is then reproducibly deposited on the working electrode using the electrodeposition technique described below. This process is set forth in U.S. Pat. No. 5,166,063, issued on Nov. 24, 1992, and tile pertinent portions thereof are hereby incorporated by reference. Bovine serum albumin is simultaneously codeposited, which results in a more stable layer. The layer is crosslinked in a glutaraldehyde solution. The entire sensor is covered with a differentially permeable biocompatible outer membrane. This proprietary membrane is two to three orders of magnitude more permeable to oxygen than glucose, thus compensating for the 'oxygen effect'. The membrane is dissolved in a solvent solution, spin-coated onto the sheet of sensors and allowed to air dry.

The final step in preparing the basic sensor involves cutting out the individual sensors. Currently, each sensor is cut out of the sheet by hand using a scalpel blade. In its finished form the implanted portion of the sensor is approximately 2.5 cm long, 0.28 mm wide and 0.06 mm thick.

To electrodeposit the enzyme coating on the electrode, a 5% by weight solution of glucose oxidase is prepared utilizing a phosphate-buffered saline solution (pH 7.4) as the solvent. While dissolving the glucose oxidase by stirring, it is important to prevent foaming of the solution which could denature the glucose oxidase. The electrodeposition cell is filled with this solution and both the electrode onto which the enzyme is to be deposited and a counter electrode are submerged inside the cell. Electrical connections are made to a galvanostat and a current is applied such that a constant current density of 5 mA/cm$^2$ results at the electrode surface. The current flow is oriented in a direction to result in a positive charge on the electrode surface to attract the negatively charged glucose oxidase molecules. The current is applied for two minutes. The actual voltage at the working electrode varies with the impedance. The electrode is removed from the enzyme solution and submerged in deionized distilled water with no agitation for five seconds to remove residual glucose oxidase. Following this, the electrode is submerged in a solution containing 2.5% by volume glutaraldehyde in phosphate-buffered saline (pH 7.4) for 30 minutes to crosslink the glucose molecules covalently together and form a water-insoluble layer. The glutaraldehyde crosslinking prevents the glucose oxidase from going back into solution. The electrode is again submerged in deionized distilled water for five seconds and allowed to dry in air for 30 minutes. The enzymatic component of the biosensor is functional at this point.

In one aspect of the invention, the working electrode of the sensor is pretreated by applying an electric current to that electrode once the electrode has been placed in the environment in which measurements will be taken. A controlled current is applied to one or more electrodes of the sensor before using the sensor to measure the presence or concentration of a substance of interest. The current is applied at a density and for a time sufficient to significantly reduce the settling time of the electrode(s). Preferably, a constant current is applied at a constant current density. However, it will be appreciated that slight variations in the current and density over the time of application will be acceptable, and that pulsing, ramping, or cycling current may be used.

The time and amount of current are selected to reduce the settling time which would be realized without such pretreatment. Typically, reductions in settling time of at least about 20% are particularly desired, with attainable reductions in settling time for certain sensors being substantially more. Any reduction in settling time is beneficial, and is therefore contemplated by the present invention. As further described herein, the settling time in some instances will reduce from 2-3 hours to about 5-10 minutes. These reductions in settling time can be especially important, for example, in acute care environments. The usefulness is also highlighted in instances in which there is a problem with a particular sensor, i.e., as to its operation or proper seating in the tissue. In other cases, a reduction of settling time from perhaps 24 hours to 1 hour would be highly beneficial.

In experiments to date, it has been preferred to use a negative current, and to apply the current at a constant density. A negative current having a density of between about 0.1 mA/cm$^2$ and about 1.0 mA/cm$^2$ is preferred, with a current density of approximately 0.5 mA/cm$^2$ being most preferred with the sensors used to date. The current is typically applied for between about one minute and about ten minutes with a pretreatment time of about two minutes being most preferred.

The settling time of the pretreated sensor is reduced from about two hours to about 10 minutes when this galvanic pretreatment is performed. This reduction of settling time is especially valuable in emergency care situations in which a two hour settling time cannot be accepted.

In another aspect of the invention, an electrochemical glucose sensor is operated using a potential which is significantly less than the 0.6 V normally applied to such sensors. It has been found that operating the sensor with a potential of between about 0.3 V and about 0.4 V significantly reduces the current created by the oxidation of compounds such as acetaminophen, and thereby minimizes the interference creaked by such compounds in the body, while having no significant effect on the magnitude of the glucose response.

Reference will now be made to specific examples using the methods described above. It is to be understood that the examples are provided to more completely describe preferred embodiments, and that no limitation to the scope of the invention is thereby intended.

EXAMPLE 1

An untreated electrochemical glucose sensor was evaluated for its "normal" settling time according to the following procedure. In this example, the settling time of the sensor was measured in vitro.

The glucose sensors were fabricated in a clean room facility following the procedure previously outlined. The resulting sensors had platinum black working and counter electrodes and a Ag/AgCl reference electrode. The surface area of the working electrode was approximately 0.1 mm$^2$. A layer of glucose oxidase and bovine serum albumin, approximately 5 $\mu$m thick, was electrodeposited on the surface of the working electrode and crosslinked with glutaraldehyde.

A proprietary outer membrane material was applied over the surface of the three electrodes. However, the present invention is not restricted to the use of a membrane or any particular membrane, the selected membrane simply being chosen as a preferred embodiment for the electrodes used in this Example.

The outer membranes were homogeneous membranes permeable to oxygen and glucose and composed of polyurethane prepared as the reaction product of diisocyanate, poly(ethylene oxide) and aliphatic diol. Membranes of this type are described in U.S. patent application Ser. No. 07/771,658, filed on Oct. 4, 1991 and entitled Hydrophilic Polyurethane Membranes for Electrochemical Glucose Sensors. The pertinent portions of this reference are hereby incorporated by reference. Such polymers are capable of absorbing from 10 to 50% of their dry weight of water, and have a ratio of the diffusion coefficient for oxygen to the diffusion coefficient for glucose of up to about 4000.

All in-vitro experiments were conducted at 37° C., maintained by a Polystat ® immersion circulator and a water bath. The output was either recorded on a two-channel strip chart recorder or collected and stored on a personal computer containing a data acquisition board capable of analog to digital (A/D) conversion. The data was simultaneously displayed on the monitor and stored on hard disk using a conventional software package.

All in-vitro tests were performed using phosphate buffered saline (PBS) as the supporting electrolyte solution. The solution had a pH value of 7.4 at 25° C. Sodium azide, 1.5 mM, was added to the PBS as a preservative. A stock glucose solution (10,000 mg/dL) was prepared from dextrose and allowed to mutarotate overnight prior to use. An aliquot of the stock solution was added to the PBS to create a solution with a glucose concentration of 100 mg/dL, which approximates the normal physiologic level. The sterile glucose solution (0.5 g/mL) used for in-vivo infusions was used as received.

To test the normal settling time of an untreated sensor, a sensor was placed in a glucose solution and an electric potential was applied to the sensor. The change in current over time was recorded arid was graphed as in FIG. 2. More particularly, the test was conducted at 37° C. in a 100 mg/dL glucose solution and a potential of +0.6 V was applied. As has been noted above, this glucose concentration is approximately equivalent to the normal physiologic level, and the potential is the same as is commonly used with such sensors.

Figure 2:
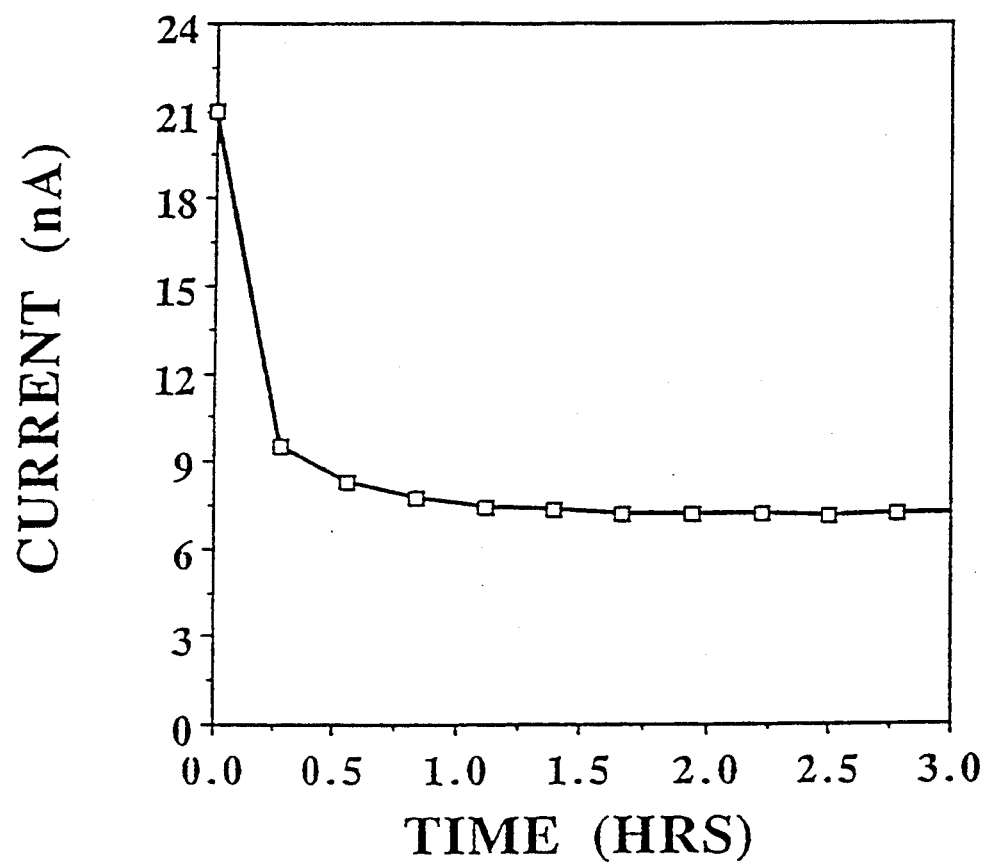
FIG. 2 is a graphical representation of the "normal" settling time of an untreated electrode, showing current output over time immediately following the initial polarization at +0.60 V for an untreated sensor in a 100 mg/dL glucose solution at 37° C.

FIG. 2 is a graph of the change in sensor current output over time as the sensor settles following initial polarization. As can be seen from the graph, the sensor appears to be fully settled approximately 1.5 hours after the application of the +0.6 V potential. Other sensors fabricated in a manner identical to the sensor used to generate FIG. 2 have been found to require between two and four hours to settle when implanted in the subcutaneous tissue of hounds, rabbits, and humans.

EXAMPLE 2

An electrochemical glucose sensor was pretreated to reduce settling time according to tile following procedure. In this example, the effect of the pretreatment was measured in vitro.

The glucose sensors were fabricated as previously outlined. The other apparatus and reagents were also provided as described in Example 1.

To evaluate galvanic pretreatment, a constant current was applied for two minutes while the sensor was in the glucose solution. A potential was then immediately applied to the sensor and the settling time was determined. Specifically, the sensor was treated with a constant current of approximately $-0.5$ mA/cm$^2$ ($-516$ nA) for two minutes prior to the application of the potential. The test was conducted at 37° C. in a 100 mg/dL glucose solution, and a potential of +0.6 V was applied after the electrode pretreatment.

Figure 3:
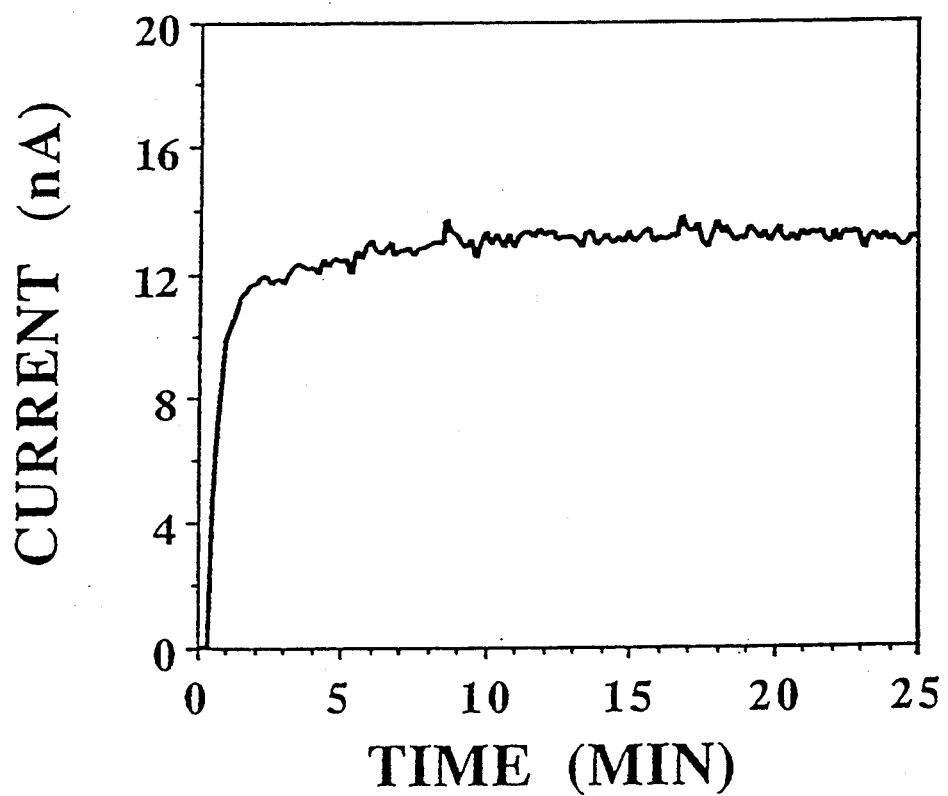
FIG. 3 is a graphical representation of the settling time of a pretreated electrode, showing current output over time immediately following initial polarization at +0.6 V for a pretreated sensor in a 100 mg/dL glucose solution at 37° C. The sensor was treated with a constant current (−516 nA) for two minutes prior to the application of the potential.

FIG. 3 is a graph of the settling time of a pretreated electrode, showing current output over time for the period immediately following the initial polarization at +0.6 V. As can be seen from the graph, the settling time of the pretreated sensor in the 100 mg/dL glucose solution was less than 10 minutes.

The amount of current applied to the sensor and the direction of current flow was optimized based on the settling time of the sensor following the galvanic pretreatment. The length of time the current was applied to the working electrode of the sensor was held constant throughout the study at two minutes. The pretreatment was found to be beneficial when the applied current was negative. The potentiostat/galvanostat used in the experiment follows the American polarity convention, so the working electrode was the anode. The counter electrode of the sensor was used as the cathode during tile pretreatment. The beneficial effect of applying a negative current to the working electrode is logical because the working electrode is also the anode when the positive potential is applied to the sensor. Conversely, it is hypothesized that a sensor based on a reduction reaction at the working electrode, such as a Clark oxygen electrode, would benefit from a galvanic pretreatment utilizing a positive current flow.

The current density was also optimized based on the performance of the tested sensor. A density of 5.0 mA/cm$^2$ was found to be too high for the sensor, resulting in a rippling of the metal conductors. Beneficial results were observed for a current density of 0.5 mA/cm$^2$ applied for two minutes as shown in FIG. 2.

EXAMPLE 3

An electrochemical glucose sensor was pretreated to reduce settling time according to the following procedure. In this example, the effect of the pretreatment was measured in vivo.

The glucose sensors were fabricated in a clean room facility following the procedure which was previously outlined. Additional apparatus and reagents were also provided as was described in the in vitro examples above.

The animal model used for these studies was the purpose-bred mixed breed hound (16–22 kg). A venous cannula to facilitate infusion of fluids and an arterial cannula for the withdrawal of blood samples for analysis were surgically implanted in the animals. The hounds were anesthetized with sodium pentobarbitol during the implantation of the sensor and the evaluation of the technique.

Prior to implantation, the sensor was placed inside one lumen of a double lumen polyethylene cannula 10 with the tip 11 previously heat-sealed shut. An opening 12 had been cut in the wall of the cannula to expose the active surfaces of electrodes 13, 14 and 15 of the sensor to the surrounding tissue once implanted (see FIG. 1). The second lumen of the cannula was filled with a piece of 27-gauge needle stock for rigidity during implantation. The entire sensor assembly was sterilized by E-beam irradiation at 2.5 MRad.

The sensors were implanted subcutaneously in the abdominal region of tile hounds. An 18-gauge needle (3.8 cm long) was inserted into the subcutaneous tissue and immediately removed to create a tunnel for the sensor. Following insertion of the sensor into this tunnel, tile 27-gauge needle stock was removed from the cannula and the sensor was taped to the skin. A custom connector was used to make electrical contact with the three leads of the sensor.

Following implantation, a $-500$ nA current (0.5 mA/cm$^2$) was applied to the working electrode for two minutes. A +0.6 V potential was immediately applied to the sensor following this pretreatment. The settling time of this sensor was less than 5 minutes as illustrated in FIG. 3.

Figure 4:
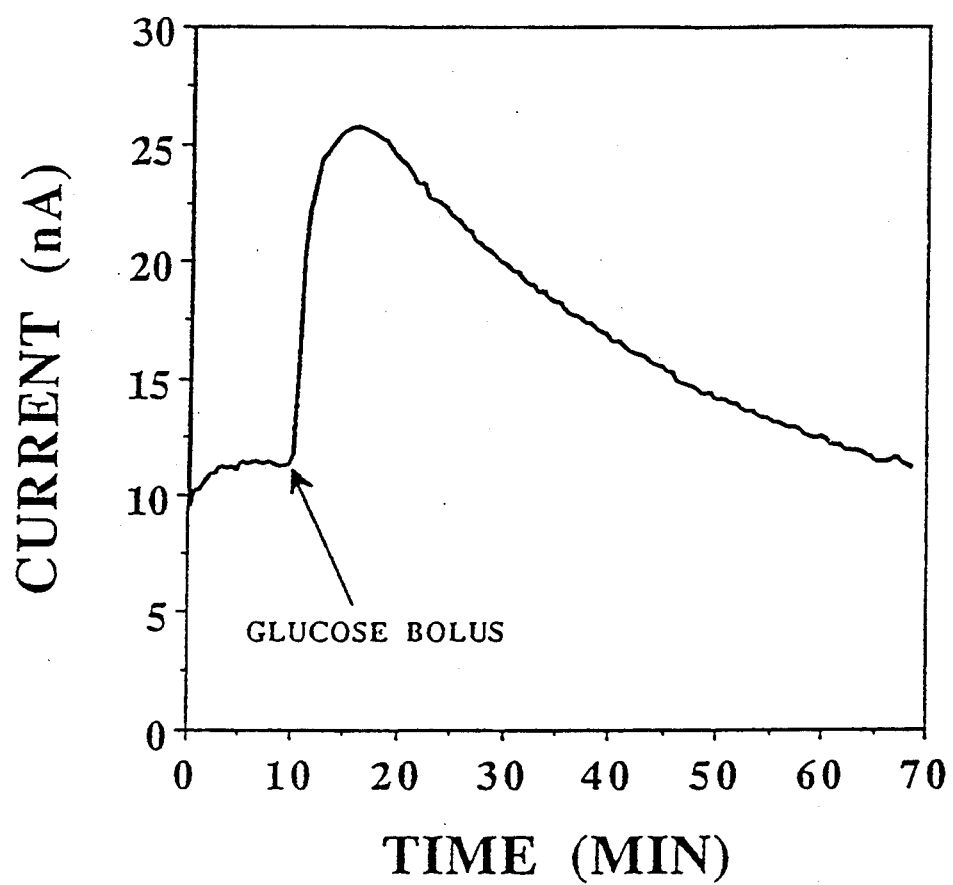
FIG. 4 is a graphical representation of current output over time immediately following initial polarization at +0.6 V for a pretreated sensor implanted in the subcutaneous tissue of an anesthetized hound. A venous glucose bolus was infused 10 minutes after polarization to demonstrate the proper function of the sensor.

Once the sensor was settled, the blood glucose concentration of the hounds was elevated by venous injection of a bolus of a sterile glucose solution (50 g of glucose per kg of hound weight) to demonstrate proper sensor function. FIG. 4 illustrates the proper function of the sensor following the bolus. Microscopic examination of the sensor following extraction from the hound revealed no deleterious effects of the treatment. In particular, no conductor delamination or membrane bubbling was observed. This procedure has been successfully repeated with 24 sensors in hounds, and with an additional four sensors in rabbits. Settling times of less than about 15 minutes were observed for pretreated sensors in all cases.

From the foregoing example, it can be seen that the application of a constant current prior to the application of the constant potential shortened the settling time of the sensor. It is hypothesized that this beneficial effect is due to the exponential drop in current during the settling of an untreated sensor having a constant potential applied thereto. For example, the current passing through the working electrode of an untreated sensor is significantly less than the current passing through the working electrode of a comparable sensor during the galvanic treatment step. In particular, from FIG. 2 it can be seen that the amount of current measured at the working electrode of the untreated sensor during the first two minutes following polarization was far less than the 500 nA applied to a comparable electrode during the two minute pretreatment step. The amount of current at the working electrode surface seemed to control the rate at which the double layer was formed and the electrodes were polarized.

It can also be seen that a difference in settling times was observed for identically prepared and pretreated sensors when used in in-vitro and in-vivo tests. For example, FIG. 3 shows an in-vitro settling time of just under 10 minutes while a settling time of about 5 minutes was observed for a sensor implanted in a hound (see FIG. 4). It is hypothesized that this difference is due to differences in impedance between the individual electrodes in the different environments.

In another aspect of the present invention, the electrochemical glucose sensor is operated at a reduced potential to minimize the effects of interfering compounds. Although glucose sensors are typically operated at a potential of about +0.6 V, interfering currents from the oxidation of compounds other than the substance of interest may be observed at such potentials. Thus it would be advantageous to develop a method of using an electrochemical sensor which minimized the current generated by the oxidation of interfering compounds without deleteriously affecting the sensitivity of the sensor to glucose. Accordingly, in this second aspect of the present invention, the sensor is operated at a potential of less than about +0.4 V to minimize the oxidation of interfering compounds such as acetaminophen. It can be seen that the sensor's sensitivity to glucose oxidation is not compromised by this method, although the sensor's sensitivity to acetaminophen oxidation is significantly reduced.

EXAMPLE 4

An electrochemical glucose sensor was operated at a reduced potential to minimize the effects of interfering compounds. In particular, the technique was evaluated for its ability to minimize the effects of acetaminophen. In this example, the effect of the technique was measured in vitro.

The glucose sensors were fabricated in the manner previously described. Additional apparatus and reagents were also provided as described in the above examples.

All in-vitro experiments were performed by placing the sensors in a 100 mL beaker filled with the PBS solution, which was submerged in constant temperature water bath set at 37° C. Glucose (100 mg/dL) and acetaminophen (4 mg/dL) solutions were created by spiking the PBS with a concentrated solution of either species. This concentration of glucose is generally equivalent to a normal physiologic glucose level, while the concentration of acetaminophen is double the normal physiologic level.

First, the current output from sensors was investigated in PBS and glucose solutions using applied potentials of +0.60 V and +0.35 V. Table 1 shows the current output from two electrochemical glucose sensors following an adequate amount of time to settle after each potential or solution concentration change. These studies show that the current output from the sensors was approximately equivalent in the 100 mg/dL glucose solution. This indicates that the lower applied potential of +0.35 V was still on the plateau of the electrochemical oxidation wave of hydrogen peroxide.

TABLE 1

| SENSOR | APPLIED POTENTIAL | PBS @ 37° C. | 100 mg/dL GLUCOSE SOLUTION @ 37° C. |
|---|---|---|---|
| 623A2 | +0.60 V | 1.0 nA | 12.1 nA |
|  | +0.35 V | 0.5 nA | 12.5 nA |
| 623A3 | +0.60 V | — | 14.2 nA |
|  | +0.35 V | — | 14.7 nA |

Table 1 also shows the baseline current in PBS at 37° C. for one of the sensors with +0.60 V and +0.35 V potentials being applied. The lower current seen with an applied potential of +0.35 V can be explained by Ohm's Law.

Figure 5:
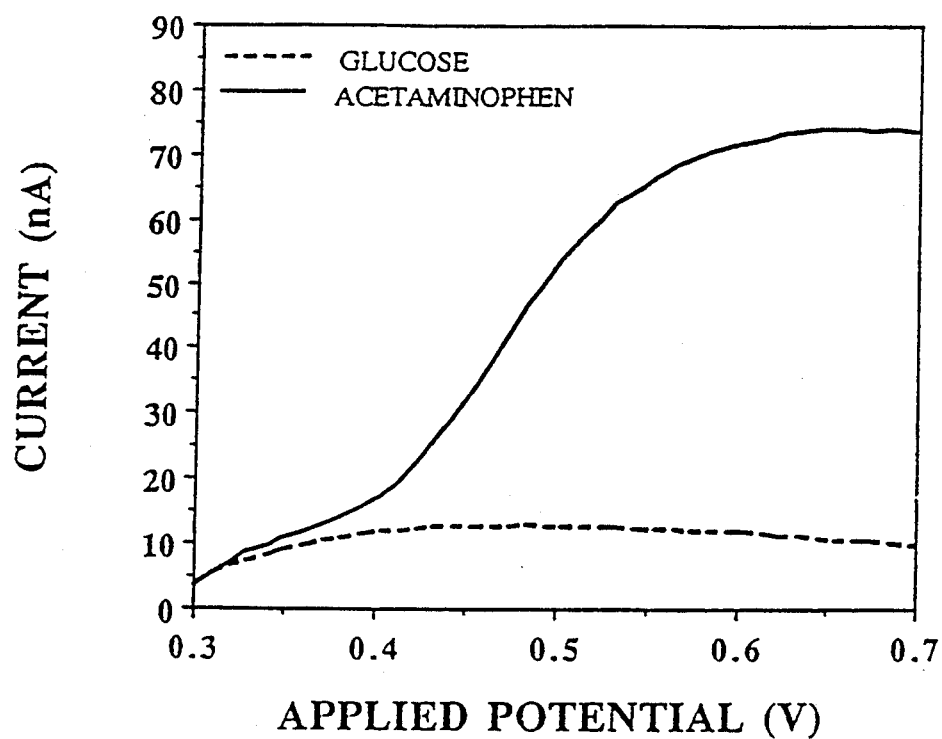
FIG. 5 shows the forward scan portion of voltammograms generated by scanning from +0.3 V to +0.7 V at 5 mV/sec in solutions of glucose (100 mg/dL) and acetaminophen (4 mg/dL) at 37° C. The background scan for the PBS buffer was subtracted from each of the voltammograms.

To further investigate the positive results observed at an applied potential of +0.35 V, cyclic voltammetry was used to select the optimal applied potential. FIG. 5 shows the forward scan portion of voltammograms for a physiologic glucose solution and an acetaminophen solution having an acetaminophen concentration of approximately double the physiologic level. The increased level of acetaminophen was used to magnify the current signal and mimic possible therapeutic usage levels. The baseline voltammogram from the PBS solution was subtracted from the glucose and acetaminophen voltammograms. The voltammograms illustrate both the desirable plateau for glucose oxidation, and the increasing current levels due to acetaminophen oxidation at higher applied potentials.

Figure 6:
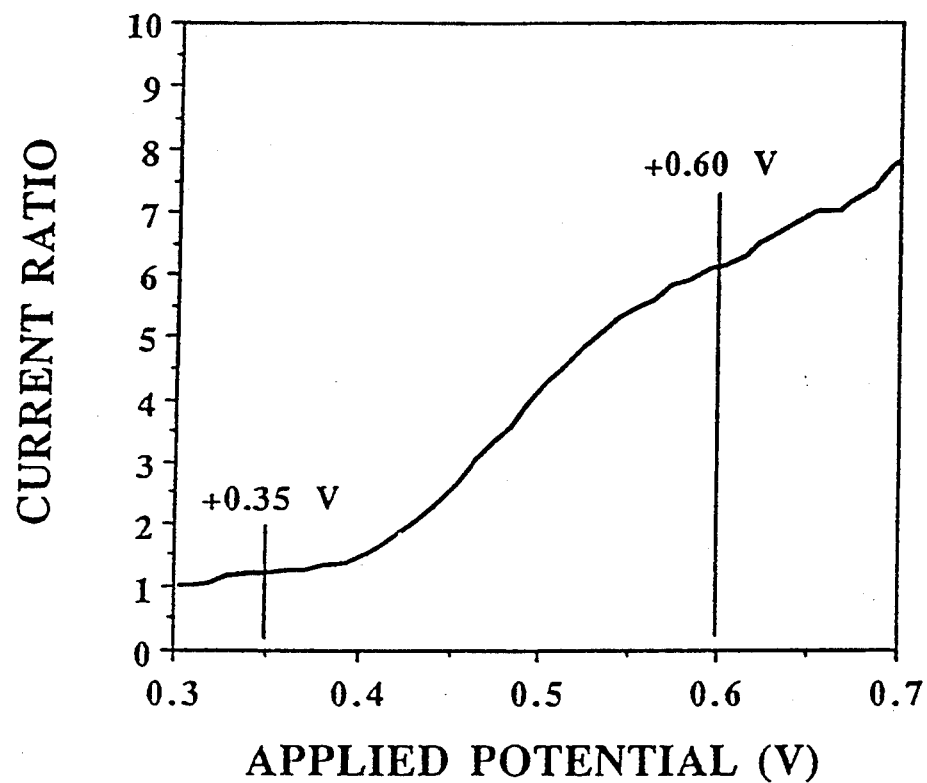
FIG. 6 is a graphical representation of the ratios of acetaminophen oxidation current to glucose (hydrogen peroxide) oxidation current over a range of applied potentials.

The selection of the optimal applied potential to detect glucose and minimize tile effects of the interfering compounds, specifically acetaminophen, was performed by examining the ratio of the acetaminophen oxidation current to glucose oxidation current as a function of applied potential. FIG. 6 illustrates this ratio as tile applied potential was varied from +0.3 to +0.7 V. From this graph it can be seen that the applied potential of +0.6 V produces more current from the oxidation of interfering compounds than are produced when a potential of +0.35 V is applied. At reduced current levels however, such as less than about +0.4 V, the current produced by the oxidation of acetaminophen is not significantly greater than the current produced by the oxidation of glucose. This graph therefore demonstrates the utility of using voltages of less than about +0.4 V to minimize the interference from other compounds.

The long-term stability of sensor function over the projected 72 hour life of the sensor is also critical to its satisfactory performance. Long-term stability of the sensor is necessary for a single calibration, either in-vitro or in-vivo, to be accurate for the entire study period. It is not expected, however, that no drift will be observed over the projected life of the sensor. Rather, it is merely necessary that such drift is within reasonable and predictable limits. The long-term drift for an electrochemical glucose sensor having a potential of +0.60 V applied thereto has previously been shown to be less than 5% over the 72 hour test period.

EXAMPLE 5

In order to demonstrate the long-term stability of sensor operation at a potential of about +0.35 V, a sensor was submerged in a glucose solution (100 mg/dL) at 37° C. and was operated at an applied potential of +0.35 V for 90 hours. The long-term drift of the sensor was observed and recorded over that time.

Figure 7:
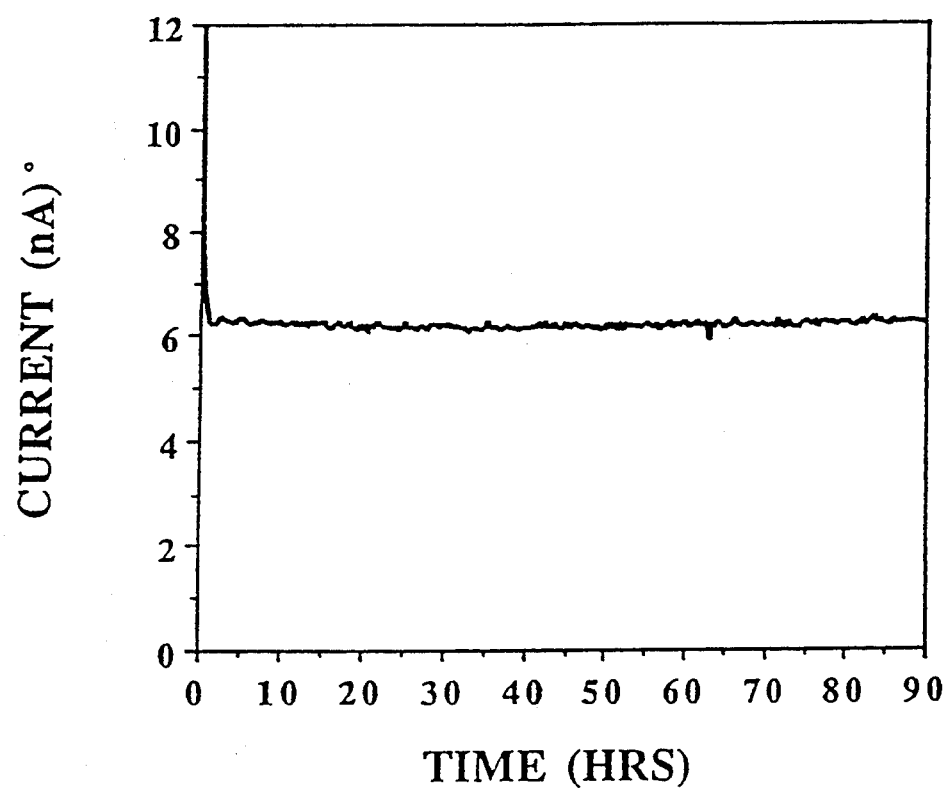
FIG. 7 is a graphical representation of the current output over time for a sensor in a 100 mg/dL glucose solution at 37° C., illustrating the long-term performance stability of a sensor when a potential of +0.35 V is applied.

FIG. 7 shows the current output from the sensor operated as above described. As can be seen from the graph, the long-term drift of the sensor under these conditions was less than 5%. Such long-term drift is within acceptable limits, and indicates that the drift in the potential of the Ag/AgCl reference electrode is not substantial enough to move the "actual" potential seen by the working electrode from the plateau for hydrogen peroxide oxidation. If the drift were substantial enough to move the potential seen by the working electrode from the plateau for hydrogen peroxide oxidation, a negative drift in the output of the sensor would have been observed.

In the following examples, an electrochemical glucose sensor is operated at a reduced potential to minimize the effects of interfering compounds. In particular, the technique is evaluated for its ability to minimize the interfering effects of acetaminophen. In these examples, the effect of the technique is measured in vivo.

The animal model used for these studies was the New Zealand white rabbit. A venous cannula to facilitate infusion of fluids and an arterial cannula for the withdrawal of blood samples for analysis were surgically implanted in the rabbits. The animals were allowed to recover before inserting the sensors so that their normal posture could be considered in the selection of the implantation site.

Prior to implantation, the sensors were placed inside one lumen of a double lumen polyethylene cannula whose tip had previously been heat-sealed shut. An opening had been cut in the wall of the cannula to expose the active electrode surfaces of the sensor to the surrounding tissue once implanted (see FIG. 1). The second lumen of the cannula was filled with a piece of 27-gauge needle stock for rigidity during implantation.

The sensors were implanted in the subcutaneous tissue between the scapulas or above the lumbar muscle area near the most posterior rib. The implantation sites were prepped with a local anesthetic, Lidocaine, prior to insertion of the sensors. An 18-gauge needle (3.8 cm long) was inserted into the subcutaneous tissue and immediately removed to create a tunnel for the sensor. Following insertion of the sensor into this tunnel, the 27-gauge needle stock was removed from the cannula and the sensor was sutured to the skin. The rabbits were kept in a restrainer during the implantation of the sensors and collection of data.

A custom connector was used to make electrical contact with the three leads of the sensor. A potential of either +0.60 V or +0.35 V was applied. In this study, the pretreatment step was not used, and the sensors were instead allowed to settle for approximately two hours following initial polarization. This allowed adequate time for the effects of the local anesthetic to subside.

Arterial blood samples were collected at 15 minute intervals throughout the duration of each glucose infusion study. The samples were centrifuged and the glucose concentration of the resulting plasma was determined. The current output from the sensor at the time of the blood sample collection was recorded and used for further analysis. The blood glucose concentrations of the rabbits were elevated by constant venous infusions of a sterile glucose solution at two different rates (15 mg/kg/min and 30 mg/kg/min).

The actual amount of current generated at the sensor from the oxidation of interfering compounds alone was determined by denaturing the glucose oxidase on the sensor prior to in-vivo implantation. The enzyme was inactivated by submersion in boiling water for 5 minutes. The inactivity was verified by an in-vitro test in a physiologic glucose solution. The effect of acetaminophen on this sensor was tested by infusion of a bolus which resulted in a concentration of about 15 mg/dL in the rabbit. This level of glucose concentration is approximately seven times the normal physiologic level.

EXAMPLE 6

The in-vivo performance of the sensor was evaluated by implanting a precalibrated (in-vitro) sensor into the subcutaneous tissue of a rabbit. A steady current output was established at a normal, basal glucose concentration level and then a concentrated glucose solution was infused to elevate the blood glucose level. Using the calibration equation from the in-vitro test, the current from the sensor in the subcutaneous tissue was converted to an apparent in-vivo glucose concentration. The plasma glucose concentration was then correlated with the apparent glucose concentration as indicated by the sensor at the time the arterial blood sample was collected.

Figure 8:
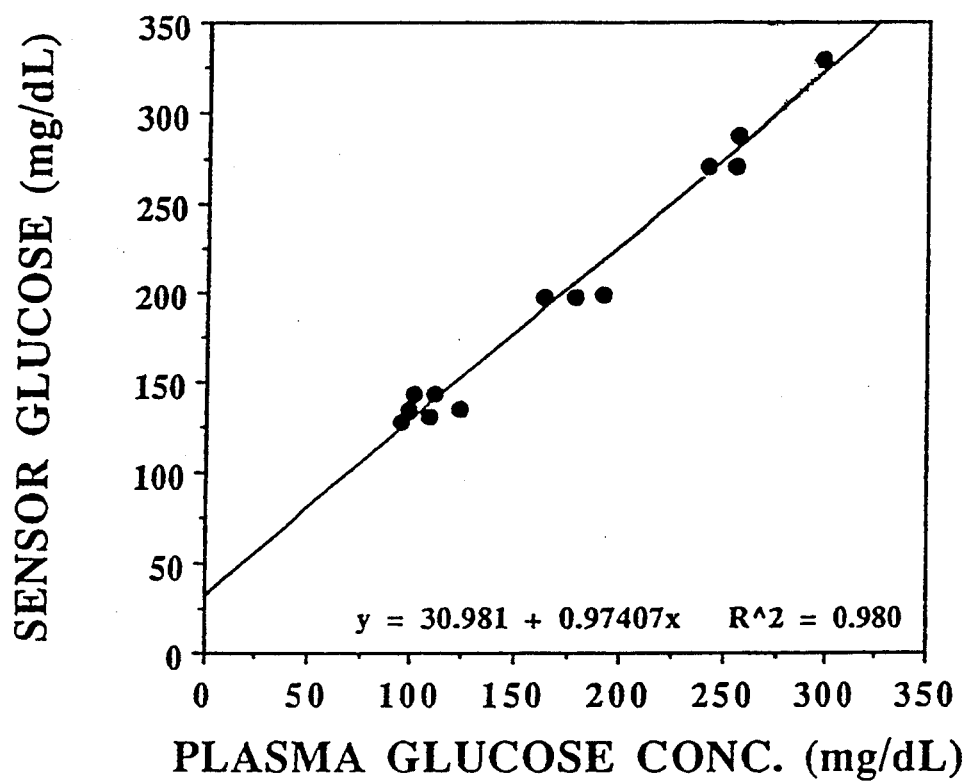
FIG. 8 is a correlation plot of plasma glucose concentration versus subcutaneous glucose concentration as measured by a sensor when a potential of +0.60 V is applied.

FIG. 8 is a correlation plot of plasma glucose concentration versus apparent glucose concentration derived from a sensor with an applied potential of +0.60 V. The sensor performance appears to be acceptable for two of three variables. The slope is approximately equal to 1.0 (m=0.97) and the response is quite linear ($R^2$=0.98). Unfortunately, there is a positive offset indicated by the y-intercept value (b=30.98 mg/dL). This offset would result in an error of approximately 30% for a physiologic glucose level of 100 mg/dL, clearly greater than the 10% error deemed acceptable by most clinicians.

Figure 9:
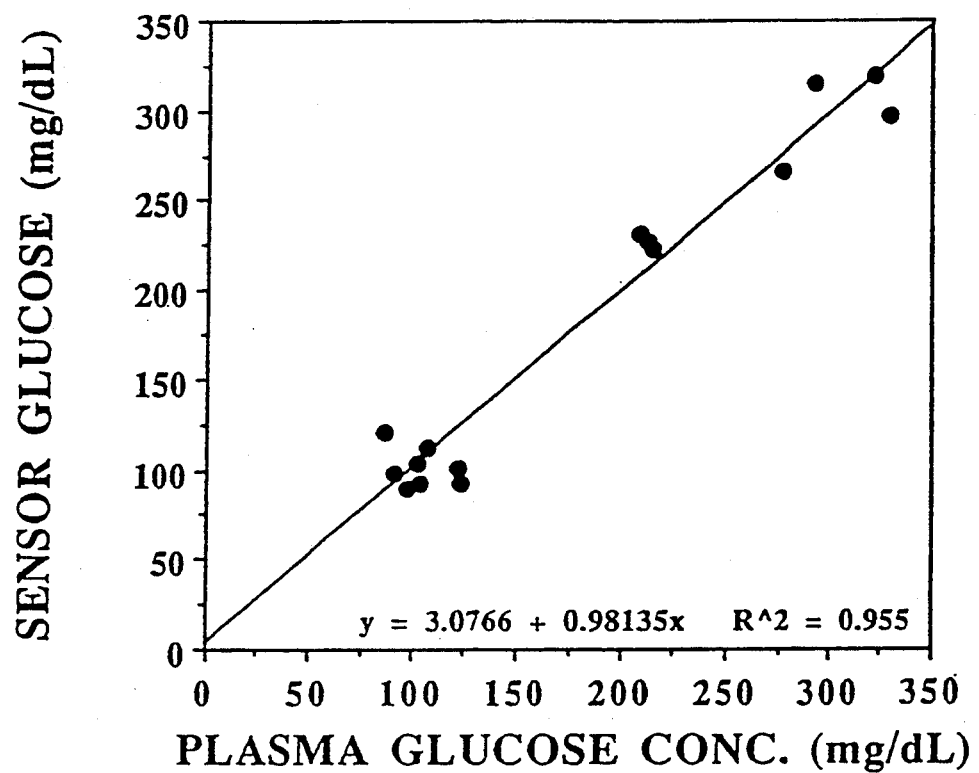
FIG. 9 is a correlation plot of plasma glucose concentration versus subcutaneous glucose concentration as measured by a sensor when a potential of +0.35 V is applied.

FIG. 9 is a correlation plot, similar to FIG. 8, except the applied potential was set at +0.35 V. This experiment utilized the same rabbit used for the generation of the data represented in FIG. 8, so the concentration of interfering compounds found in-vivo could be assumed to be similar in each study. The in-vivo performance of this sensor was acceptable since the offset (y-intercept)

was decreased to 3 mg/dL, while the linear correlation and near-unity slope were retained. This experiment suggests that the current created by the oxidation of interfering compounds in-vivo can be decreased to an acceptable level without the use of additional exclusion membranes, electrodes, enzymes, or mediators. In addition, the excellent correlation shown between the plasma glucose values and the glucose concentration measured in the subcutaneous tissue by the sensor substantiates the validity and accuracy of monitoring glucose values in the subcataneous tissue.

EXAMPLE 7

To further test this hypothesis, a sensor identical to those used in the aforementioned experiments was placed in boiling water to denature the glucose oxidase. This process rendered the enzyme inactive and assured that none of the current generated by the sensor would be due to glucose. Instead, the output would be the combination of only the background and interferent oxidation currents.

Table 2 shows the in-vivo current from a typical sensor having its glucose oxidase layer inactivated. The "baseline" current generated with the potential of +0.60 V is higher than the in-vitro baseline current value normally seen in PBS as illustrated in Table 1. This difference of approximately 3.5 nA is believed to be due to the oxidation of interferents at the working electrode. In contrast, when the applied potential was decreased to +0.35 V, this same sensor had a current output of 0.6 nA. This current value, which is approximately equal to the in-vitro baseline current value in PBS for +0.35 V shown in Table 1, further proves that lowering the applied potential decreases the contribution, and resulting error, from the oxidation of interfering compounds.

TABLE 2

| APPLIED POTENTIAL | BASELINE CURRENT | CURRENT INCREASE FROM ACETAMINOPHEN BOLUS (15 mg/dL) |
| --- | --- | --- |
| +0.60 V | 4.5 nA | 9.0 nA |
| +0.35 V | 0.6 nA | 0.5 nA |

EXAMPLE 8

Further evidence was generated by infusing an acetaminophen bolus into the venous cannula of the rabbit and monitoring the response of the sensor. The bolus increased the acetaminophen concentration in the rabbit by approximately 15 mg/dL, roughly seven times the normal physiologic level. The large bolus was given to account for the possibility that a portion of the drug would be metabolized prior to diffusion into the subcutaneous tissue. As is shown in Table 2, the increase in current output from the sensor following identical infusions of acetaminophen was quite different for tile two applied potential values. The increase in current due to the acetaminophen bolus for an applied potential value of +0.60 V was approximately 18 times the increase in current measured when a potential of only +0.35 V was applied to the sensor.

The above-described examples show that by decreasing the applied potential from +0.60 V to +0.35 V for an amperometric electroenzymatic glucose sensor designed for in-vivo applications, the effect of interfering compounds can be decreased greatly without affecting the response to glucose. This is accomplished without the necessity of additional membrane layers, electrodes, enzymes or mediators. Experiments conducted in-vitro demonstrated this technique to be viable for reducing the effect of acetaminophen. In-vivo experiments, which were inclusive of all biologically occurring interferents, have substantiated this finding.

A number of variations are contemplated and may be included to adapt the invention described in the above embodiments without changing the basic invention. Therefore, while the invention has been illustrated and described in detail in the foregoing examples, the same are to be considered illustrative and not restrictive in character. It is to be understood that the preferred embodiments have been shown and described, and that all changes and modifications that come within the spirit of the invention are desired to be protected.

We claim:

1. A method of reducing the settling time of an electrochemical sensor having one or more electrodes, comprising:
   pretreating the electrochemical sensor after placement in a medium by applying a controlled electric current to one or more of the electrodes of the sensor before using the sensor to measure the presence or concentration of a substance of interest; wherein the controlled current is applied at a density and for a time to reduce the settling time of the electrode to less than about 25 minutes.

2. The method of claim 1 in which the pretreating comprises applying a constant electric current.

3. The method of claim 1 in which the electric current is applied to reduce the settling time of the electrode to less than about 15 minutes.

4. The method of claim 1 wherein the current density is a constant current density between about 0.1 mA/cm$^2$ and about 1.0 mA/cm$^2$ during said pretreatment.

5. The method of claim 4 wherein the constant current density is approximately 0.5 mA/cm$^2$ during said pretreatment.

6. The method of claim 1 wherein the current is applied at a constant density for between about one minute and about ten minutes during said pretreatment.

7. The method of claim 6 wherein the current is applied at a constant density for approximately two minutes during said pretreatment.

8. The method of claim 1 wherein the current is a negative current.

9. A method of measuring the concentration of glucose in a liquid medium, comprising the steps of:
   contacting a glucose-containing medium with an electrochemical sensor having an electrode;
   pretreating the electrode by applying a controlled electric current to the electrode at a current density and for a time to reduce the settling time of the electrode to less than about 25 minutes; and subsequently
   operating the sensor by applying a constant electric potential to the electrode;
   measuring the rate of current change as $H_2O_2$ is produced from glucose, oxygen and water at the electrode; and
   translating the rate of current change to a value of glucose concentration.

10. The method of claim 9 in which the pretreating comprises applying a constant electric current.

11. The method of claim 9 in which tile electric current is applied to reduce the settling time of the electrode to less than about 15 minutes.

12. The method of claim 11 wherein the current density is a constant density between about 0.1 mA/cm$^2$ and about 1.0 mA/cm$^2$ during said pretreatment.

13. The method of claim 12 wherein tile constant density is approximately 0.5 mA/cm$^2$ during said pretreatment.

14. The method of claim 11 wherein the current is applied at a constant density for between about one minute and about ten minutes during said pretreatment.

15. The method of claim 14 wherein the current is applied at a constant density for approximately two minutes during said pretreatment.

16. The method of claim 11 wherein the current is a negative current.

17. The method of claim 11 wherein said contacting step comprises contacting a glucose-containing medium with an electrochemical sensor having a platinum black working electrode, a platinum black counter electrode, and an Ag/AgCl reference electrode.

18. A method of measuring the concentration of glucose in a liquid medium, comprising the steps of:
contacting a glucose-containing medium with an electrochemical sensor, said sensor having a working electrode, a counter electrode and a reference electrode;
applying an electric potential greater than about 0.10 V and less than about 0.40 V to the working electrode;
measuring the rate of current change as H$_2$O$_2$ is produced from glucose, oxygen and water at the working electrode of the sensor; and
translating the rate of current change to a value of glucose concentration.

19. The method of claim 18 wherein the applied electric potential is approximately +0.35 V.

20. The method of claim 18 wherein the glucose-containing medium also contains interfering compounds.

21. The method of claim 20 wherein the glucose-containing medium also contains acetaminophen as an interfering compound.

22. The method of claim 18 wherein the working electrode is the anode, and the counter electrode is the cathode.

23. The method of claim 18 wherein said contacting step comprises contacting a glucose-containing medium with an electrochemical sensor having a platinum black working electrode, a platinum black counter electrode, and an Ag/AgCl reference electrode.

24. A method of measuring the concentration of glucose in a liquid medium, comprising the steps of:
contacting a glucose-containing medium with an electrochemical sensor having an electrode;
pretreating the electrode by applying a controlled electric current to the electrode at a density and for a time to reduce the settling time of the electrode to less than about 25 minutes; and subsequently
operating the sensor by applying a constant electric potential greater than about 0.1 V and less than about 0.40 V to the working electrode of the sensor;
measuring the rate of current change as H$_2$O$_2$ is produced from glucose, oxygen and water at the working electrode of the sensor; and
translating the rate of current change to a value of glucose concentration.

25. The method of claim 24 in which the pretreating comprises applying a constant electric current.

26. The method of claim 24 in which the electric current is applied to reduce the settling time of the electrode to less than about 15 minutes.

27. The method of claim 24 wherein the current density is a constant current density between about 0.1 mA/cm$^2$ and about 1.0 mA/cm$^2$ during said pretreatment.

28. The method of claim 27 wherein the constant current density is approximately 0.5 mA/cm$^2$ during said pretreatment.

29. The method of claim 24 wherein the current is applied at a constant density for between about one minute and about ten minutes during said pretreatment.

30. The method of claim 24 wherein the applied electric potential is approximately +0.35 V.

31. The method of claim 24 wherein said contacting step comprises contacting a glucose-containing medium with an electrochemical sensor having a working electrode with glucose oxidase deposited thereon.

* * * * *